United States Patent
Liu

(10) Patent No.: US 7,534,907 B2
(45) Date of Patent: May 19, 2009

(54) ABSORBABLE α-CYANOACRYLATE COMPOSITIONS

(75) Inventor: Hongbo Liu, Hillsborough, NJ (US)

(73) Assignee: Ethichon, Inc., Somerville, NJ (US)

( * ) Notice: Subject to any disclaimer, the term of this patent is extended or adjusted under 35 U.S.C. 154(b) by 0 days.

(21) Appl. No.: 11/755,093

(22) Filed: May 30, 2007

(65) Prior Publication Data

US 2007/0224163 A1 Sep. 27, 2007

Related U.S. Application Data

(62) Division of application No. 11/088,587, filed on Mar. 24, 2005, now Pat. No. 7,238,828.

(51) Int. Cl.
*A61K 31/785* (2006.01)
*C07C 255/19* (2006.01)
*C08G 63/91* (2006.01)
*C08G 63/48* (2006.01)

(52) U.S. Cl. .................... 558/442; 558/441; 424/78.27; 525/54.1

(58) Field of Classification Search ................. 558/441, 558/442; 424/78.27; 525/54.1
See application file for complete search history.

(56) References Cited

U.S. PATENT DOCUMENTS

| | | | |
|---|---|---|---|
| 3,940,362 A | | 2/1976 | Overhults |
| 3,995,641 A | | 12/1976 | Kronenthal et al. |
| 4,313,865 A | | 2/1982 | Teramoto et al. |
| 4,560,723 A | | 12/1985 | Millet et al. |
| 4,720,513 A | * | 1/1988 | Kameyama et al. |
| 5,259,835 A | * | 11/1993 | Clark et al. |
| 5,328,687 A | | 7/1994 | Leung et al. |
| 5,514,371 A | | 5/1996 | Leung et al. |
| 5,514,372 A | * | 5/1996 | Leung et al. |
| 5,575,997 A | | 11/1996 | Leung et al. |
| 5,582,834 A | | 12/1996 | Leung et al. |
| 5,624,669 A | | 4/1997 | Leung et al. |
| 5,928,611 A | | 7/1999 | Leung |
| 6,010,714 A | | 1/2000 | Leung et al. |
| 6,143,352 A | * | 11/2000 | Clark et al. |
| 6,372,313 B1 | * | 4/2002 | D'Alessio et al. |
| 6,425,704 B2 | * | 7/2002 | Voiers et al. |
| 6,428,233 B1 | * | 8/2002 | Clark et al. |
| 6,455,064 B1 | * | 9/2002 | Narang et al. |
| 6,512,023 B1 | | 1/2003 | Malofsky et al. |
| 6,579,469 B1 | | 6/2003 | Nicholson et al. |
| 6,620,846 B1 | | 9/2003 | Jonn et al. |
| 6,802,416 B1 | * | 10/2004 | D'Alessio et al. |

FOREIGN PATENT DOCUMENTS

| | | | |
|---|---|---|---|
| JP | 08505383 T2 | | 6/1996 |
| WO | WO 99/55374 | * | 11/1999 |
| WO | WO 99/55394 | * | 11/1999 |
| WO | WO 00/26284 | * | 5/2000 |

OTHER PUBLICATIONS

Paez et al. J. Mat. Science: Materials in Medicine 2004, 15, 109-115.*
Margules et al. Med. & Biol. Eng. & Comput. 1980, 18, 549-553.*
http://medical.merriam-webster.com/medical/cyanoacrylate.*
International Search Report PCT/US2006/010348 (ETH 5189WOPCT) Int. mailed Aug. 3, 2006.

* cited by examiner

*Primary Examiner*—Kamal A Saeed
*Assistant Examiner*—Jason M Nolan
(74) *Attorney, Agent, or Firm*—David R. Crichton

(57) ABSTRACT

A monomer composition comprising at least one polymerizable alkyl ester α-cyanoacrylate monomer. Specifically, the α-cyanoacrylate monomer is an alkyl ester α-cyanoacrylate monomer of the general formula having a spacer R1:

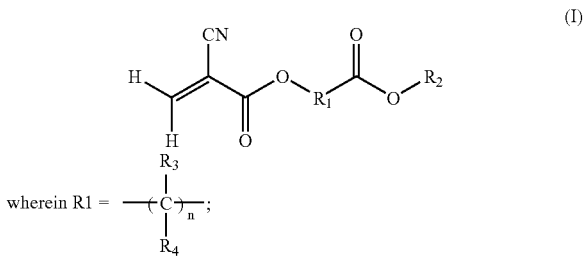

n is from 2 to 12; R3 and R4 are each an alkyl group or a hydrogen, and at least one of R3 or R4 is an alkyl group (e.g. linear or branched, or cyclic) having from 1, 2, 3, 4, 5, 6, 7, 8, 9, 10, 11, 12 and 13 carbon atoms; R2 is an alkyl group (e.g. linear or branched, or cyclic) having from 1, 2, 3, 4, 5, 6, 7, 8, 9, 10, 11, 12 and 13 carbon atoms; and the combined number of carbon atoms (N) in the spacer R1 is at least n+1.

1 Claim, 2 Drawing Sheets

Figure 1.  Lap shear joint sample

ABSORBABLE α-CYANOACRYLATE COMPOSITIONS

This application is a Divisional of U.S. application Ser. No. 11/088587 filed on 24 Mar. 2005, which issued into U.S. Pat. No. 7,238,828. The complete disclosure of the aforementioned related U.S. patent is hereby incorporated herein by reference for all purposes.

BACKGROUND OF THE INVENTION

1. Field of the Invention

The invention relates to a new class of α-cyanoacrylate monomers which are useful as adhesives or sealants, and more particularly to compounds which are alkyl ester α-cyanoacrylate monomers. This invention further relates to the use of such alkyl ester α-cyanoacrylates monomers in α-cyanoacrylate compositions that are useful as tissue adhesives/sealants in surgical, medical and industrial applications, and to the production thereof.

2. State of the Art

Monomer and polymer adhesives/sealants are used in both industrial (including household) and medical/surgical applications. Included among these adhesives or sealants are the α-cyanoacrylates monomers and polymers resulting therefrom. Since the discovery of the adhesive/sealant properties of such monomers and polymers, they have found wide use due to the speed with which they cure, the strength of the resulting bond formed, and their relative ease of use. These characteristics have made α-cyanoacrylate compositions the primary choice for numerous adhesive applications such as bonding plastics, rubbers, glass, metals, wood, and, more recently, medical, biological or living tissues.

Medical and surgical applications of α-cyanoacrylate compositions include their use as alternates or adjuncts to surgical sutures, meshes and staples or other medical devices in wound closure, as well as for covering and protecting surface wounds such as lacerations, abrasions, burns, stomatitis, sores, and other surface wounds. When an α-cyanoacrylate composition is applied, it is usually applied in its monomeric form, and the resultant polymerization gives rise to the desired adhesive bond or sealant strength.

For example, polymerizable α-cyanoacrylate monomers and compositions comprising such monomers are disclosed in U.S. Pat. No. 5,328,687 to Leung et al. Suitable methods for applying such compositions to substrates, and particularly in medical applications, are described in, for example, U.S. Pat. Nos. 6,620,846 B1, 6,512,023B1, and 3,995,641, the contents each of which is incorporated by reference herein in its entirety.

U.S. Pat. No. 5,928,611 to Leung broadly discloses α-cyanoacrylate monomers having a large number of possible substituent groups. The disclosure focuses on α-cyanoacrylate monomers, with alternative representation of ester cyanoacrylate monomers having an organic radical substituent. However, the disclosure does not specify particular properties, such as absorbability, possessed by polymers formed with particular cyanoacrylate monomers.

U.S. Pat. No. 3,995,641 to Kronenthal et al. discloses carbalkoxyalkyl α-cyanoacrylate monomers that form absorbable polymer adhesives in mammalian tissue. Under some circumstances, absorbable polymer adhesives/sealants have benefits over non-absorbable polymer adhesives/sealants, particularly for some medical applications. However, some α-cyanoacrylate monomers have particularly slow reaction kinetics which reduce their practical value as surgical adhesives/sealants.

Therefore, there is still a need for α-cyanoacrylate compositions that exhibit a rapid cure rate sufficient for medical applications and produce an absorbable polymer adhesive/sealant. It is also desirable to have a monomer based internal adhesive or sealant composition that is capable of polymerizing in vivo to form an internal adhesive or sealant, in order to provide an opportunity for manipulation and re-alignment. Specifically, it is desirable that the adhesive or sealant composition fill internal cavities and voids, penetrating and conforming to the interstices and pores of the tissue, prior to curing or setting.

Additionally, it is desirable to have a monomer based internal adhesive or sealant composition that polymerizes in vivo, where the monomer, the composition thereof, and the resultant polymer are biocompatible. The resultant polymer should also be biodegradable.

Finally, it is desirable that the degradation products of the resultant polymer be both biocompatible and water soluble, so that the degradation products are completely eliminated from the human body as waste products.

SUMMARY OF THE INVENTION

Figure 1:
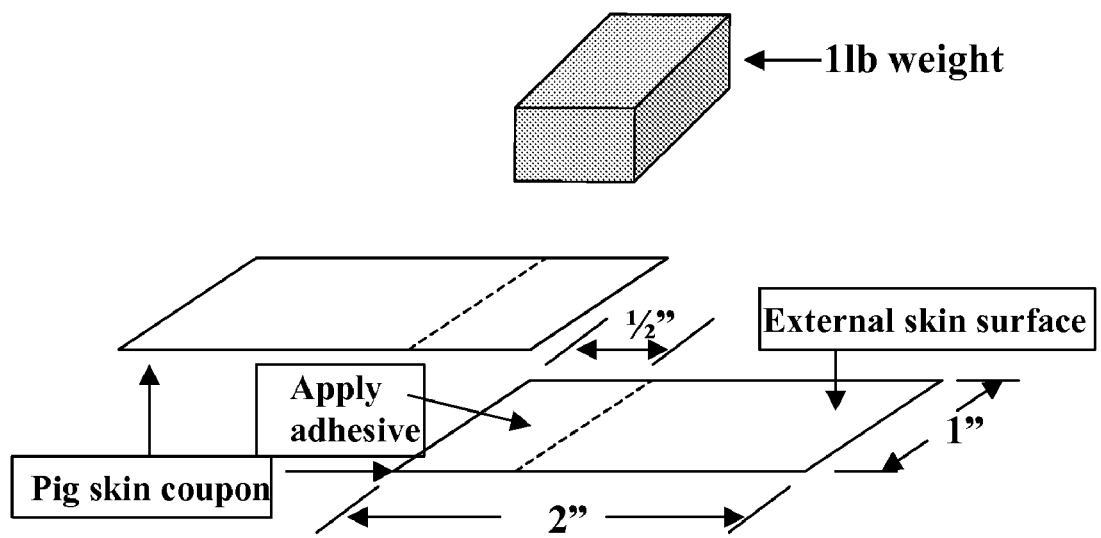
FIG. 1 is a schematic representation of lap shear joint

The present invention relates to a monomer composition comprising at least one alkyl ester α-cyanoacrylate monomer, that polymerizes to form an adhesive or sealant possessing exceptional adhesive/sealant characteristics, and is minimally toxic to non-toxic, and absorbable by living organisms.

The α-cyanoacrylate monomers of the present invention are alkyl ester α-cyanoacrylate monomers of the general formula having a spacer R1:

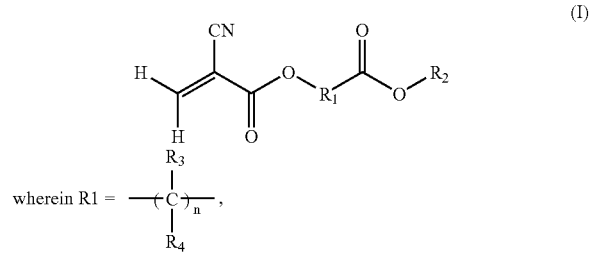

wherein n is from 2 to 12; R3 and R4 is an alkyl group or a hydrogen, and at least one of R3 or R4 is an alkyl group (e.g. linear or branched, or cyclic) having from 1, 2, 3, 4, 5, 6, 7, 8, 9, 10, 11, 12 and 13 carbon atoms; R2 is an alkyl group (e.g. linear or branched, or cyclic) having from 1, 2, 3, 4, 5, 6, 7, 8, 9, 10, 11, 12 and 13 carbon atoms; and the combined number of carbon atoms (N) in the spacer R1 is at least n+1.

The present invention also provides a kit, comprising a saleable package comprising a first container that contains at least one alkyl ester α-cyanoacrylate monomer; and optionally a polymerization initiator or accelerator in an amount effective to initiate the polymerization.

The present invention additionally provides a method of closing living tissue, comprising applying to living tissue a monomer composition comprising at least one alkyl ester α-cyanoacrylate monomer and optionally a polymerization initiator or accelerator in an amount effective to accelerate the polymerization and to achieve satisfactory mechanical performance of the resulting polymer.

The present invention also provides a method of treating living tissue, comprising determining a desired rate at which an adhesive/sealant polymer is absorbed; optionally selecting a suitable combination of monomer and polymerization initiator or accelerator to provide the desired absorption rate; and optionally applying to living tissue the polymerization initiator or accelerator and monomer to form an absorbable polymer adhesive.

DETAILED DESCRIPTION OF PREFERRED EMBODIMENTS

For the purposes of this invention, the term "absorbable" means capable of being absorbed, degraded or biodegraded, either fully or partially, by animal (including human) tissue after application of the adhesive or sealant.

For the purposes of this invention, the term "substantially absorbed" means at least 90% absorbed.

Monomer compositions of the present invention, and polymers formed therefrom are useful as tissue adhesives, covering for open wounds, and in other biomedical applications. More particularly, they find use in, for example, approximating tissue; apposing surgically incised or traumatically lacerated tissues; dressing burns, skin or other superficial or deep tissue surface wounds (such as abrasions, chaffed or raw skin, and/or stomatitis); and aiding repair and regrowth of living tissue.

Monomer compositions of the present invention, and polymers formed therefrom, have broad application for sealing wounds in various living tissue, internal organs and blood vessels; sealing wounds to retard or prevent bleeding; preventing body fluid leakage; and can be applied, for example, on the interior or exterior of blood vessels and various organs or tissues.

The monomer composition of the present invention comprise at least one polymerizable alkyl ester α-cyanoacrylate monomer. Specifically, the α-cyanoacrylate monomer is an alkyl ester α-cyanoacrylate monomer of the general formula having a spacer R1:

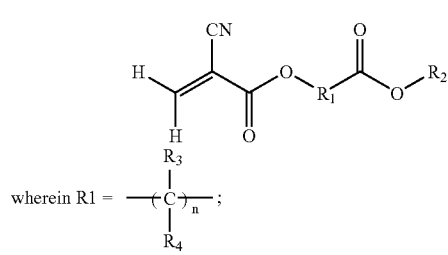

(I)

wherein R1 = n is from 2 to 12; R3 and R4 are each an alkyl group or a hydrogen, and at least one of R3 or R4 is an alkyl group (e.g. linear or branched, or cyclic) having from 1, 2, 3, 4, 5, 6, 7, 8, 9, 10, 11, 12 and 13 carbon atoms; R2 is an alkyl group (e.g. linear or branched, or cyclic) having from 1, 2, 3, 4, 5, 6, 7, 8, 9, 10, 11, 12 and 13 carbon atoms; and the combined number of carbon atoms (N) in the spacer R1 is at least n+1.

It is important that the value of n is in a range such that it allows for feasible preparation and purification of the composition while providing desirable biodegradability and adhesive properties. A preferred range for n is from about 2 to 12, a more preferred range is from about 2 to 8.

The combined number of carbon atoms (N) is defined as the combined value of the number of carbon atoms on the R3 and R4 side branches and the number of carbon atoms on the spacer backbone (n), wherein the combined number of carbon atoms (N) in

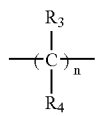

is at least n+1.

A preferred combined number of carbon atoms (N) in

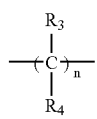

is 4 or greater.

A more preferred combined number of carbon atoms (N) in

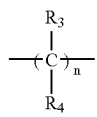

is 5 or greater.

Examples of the monomers include, but are not limited to:

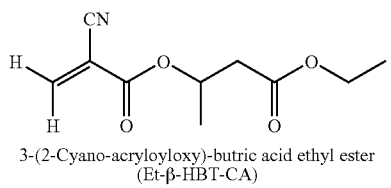

(II)

3-(2-Cyano-acryloyloxy)-butric acid ethyl ester (Et-β-HBT-CA)

3-(2-Cyano-acryloyloxy)-butric acid ethyl ester Et-β-HBT-CA)

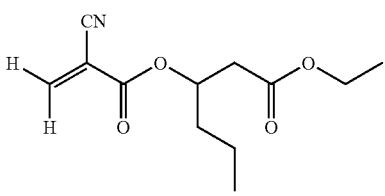

(III)

3-(2-Cyano-acryloyloxy)-hexanoic acid ethyl ester (Et-β-CPL-CA)

3-(2-Cyano-acryloyloxy)-hexanoic acid ethyl ester (Et-β-CPL-CA)

The alkyl ester cyanoacrylate monomers described herein can be prepared according to the procedure described in U.S. Pat. No. 3,995,641 to Kronenthal et al., which is hereby incorporated by reference. In the Kronenthal et al. method, such cyanoacrylate monomers are prepared by reacting an alkyl ester of an alpha-cyanoacrylic acid with a cyclic 1,3-diene to form a Diels-Alder adduct, which is then subjected to alkaline hydrolysis followed by acidification to form the corresponding alpha-cyanoacrylic acid adduct. The alpha-cyanoacrylic acid adduct is preferably esterified by an alkyl bromoacetate to yield the corresponding carbalkoxymethyl alpha-cyanoacylate adduct. Alternatively, the alpha-cyanoacrylic acid adduct may be converted to the alpha-cyanoacrylyl halide adduct by reaction with thionyl chloride. The alpha-cyanoacrylyl halide adduct is then reacted with an alkyl hydroxyacetate or a methyl substituted alkyl hydroxyacetate to yield the corresponding carbalkoxymethyl alpha-cyanoacrylate adduct or carbalkoxy alkyl alpha-cyanoacrylate adduct, respectively. The cyclic 1,3-diene blocking group is finally removed and the carbalkoxy methyl alpha-cyanoacrylate adduct or the carbalkoxy alkyl alpha-cyanoacrylate adduct is converted into the corresponding carbalkoxy alkyl alpha-cyanoacrylate by heating the adduct in the presence of a slight deficit of maleic anhydride.

The alkyl ester α-cyanoacylate monomers can also be prepared through the Knoevenagel reaction of an alkyl cyanoacetate, or an alkyl ester cyanoacetate, with paraformaldehyde. This leads to a cyanoacrylate oligomer. Subsequent thermal cracking of the oligomer results in the formation of a cyanoacrylate monomer. After further distillation, a cyanoacrylate monomer with high purity (greater than 95.0%, preferably greater than 99.0%, and more preferably greater than 99.8%) may be obtained.

Monomers prepared with low moisture content and essentially free of impurities (e.g., surgical grade) are preferred for biomedical use.

The alkyl ester α-cyanoacrylate monomer may be employed individually or as a comonomer with one or more alkyl ester α-cyanoacrylate monomer or other monomers such as alkyl cyanoacrylate and alkoxyalkyl cyanoacrylate including, but not limited to, methyl cyanoacrylate, ethyl cyanoacrylate, n-butyl cyanoacrylate, isobutyl cyanoacrylate, n-octyl cyanoacrylate, 2-octyl cyanoacrylate, dodecyl cyanoacrylate, 2-ethylhexyl cyanoacrylate, methoxyethyl cyanoacrylate, 2-ethoxyethyl cyanoacrylate, 3-methoxybutyl cyanoacrylate, 2-butoxyethyl cyanoacrylate, 2-isopropoxyethyl cyanoacrylate, and 1-methoxy-2-propyl cyanoacrylate.

In the event the alkyl ester α-cyanoacrylate monomers have a slow polymerization rate, an effective agent which initiates or accelerates polymerization of the alkyl ester cyanoacrylate monomer may be used with the monomer composition. Initiators and accelerators particularly suitable for use with alkyl ester α-cyanoacrylates provide a faster cure rate while retaining the absorbable properties of the adhesive. Alkyl ester α-cyanoacrylate monomers stimulated to cure by a suitable initiator or accelerator may be made to cure in as short as a few seconds to a few minutes. The cure rate may be closely controlled by selection of an amount or concentration of initiator or accelerator added to the monomer composition and may thus be readily controlled by one skilled in the art in light of the present disclosure. A suitable initiator provides a consistent controllable complete polymerization of the monomer so that the polymerization of the monomer can be made to occur in the time desired for the particular application.

Initiators or accelerators are molecules (organic or inorganic or hybride thereof) having nucleophilic functionalities. Such functionalities include but not limited to nitrogen containing groups (e.g., amino, imine, amide, imide), phosphor containing compounds (e.g., phosphine), oxygen containing compounds (e.g., hydroxyls, carboxylate, water), sulfur containing compounds (such as thiols). Examples of effective inorganic initiators or accelerators include but not limited to NaCl, NaHCO$_3$, Na$_2$CO$_3$ and sodium phosphates. Examples of organic-inorganic hybride initiators or accelerators include but not limited to metallo-organic compounds, such as Grinard agents. Suitable initiators or accelerators are described in, for example, U.S. Pat. No. 6,620,846 B1, the content is incorporated by reference herein in its entirety.

Quaternary amine initiators or accelerators are also known to be effective. In preferred embodiments, the present invention provides for the use of quaternary amine polymerization initiators or accelerators such as quaternary amines having the formula:

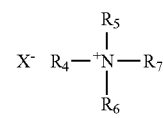

wherein R4, R5, R6 and R7 are each independently H or a substituted or unsubstituted straight, branched or cyclic alkyl group; a substituted or unsubstituted aromatic ring; a substituted or unsubstituted aralkyl group; or a substituted or unsubstituted alkyl or aromatic group which may include one or more hetero atom functionalities such as oxygen, sulfur, nitrogen, etc.; and X⁻ is an anion such as a halide, for example chloride, bromide, or fluoride, or hydroxyl. In preferred embodiments, at least one of R4, R5, R6 and R7 includes an aromatic group and/or a hetero atom functionality such as an ether or ester linkage or corresponding linkages where the hetero atom is sulfur or nitrogen. Preferred quaternary amine initiators are selected from the group consisting of domiphen bromide, butyrylcholine chloride, benzalkonium bromide and acetyl choline chloride.

Initiators may be in the form of a solid, such as a powder or a solid film, or in the form of a liquid, such as a viscous or paste-like material. The initiator or accelerator may also include a variety of additives, such as surfactants or emulsifiers. Preferably, the initiator or accelerator is soluble in the monomer composition, and/or comprises or is accompanied by at least one surfactant which, in embodiments, helps the initiator or accelerator co-elute with the monomer composition. In embodiments, the surfactant may help disperse the initiator or accelerator in the monomer composition.

The initiator or accelerator may be applied to tissue before the monomer composition, or may be applied directly to the monomer composition once the monomer composition is applied to tissue. In embodiments, the initiator or accelerator may be combined with the monomer composition just prior to applying the composition to tissue.

The selection of an initiator or accelerator may additionally affect the rate at which the polymerized monomer is absorbed by living tissue. Therefore, the most suitable initiators or accelerators are those that polymerize the monomer at a rate suitable for medical applications while providing a polymer that is substantially absorbed in less than two years. Preferable initiators are those that absorb water as the absorption of water encourages the degradation of the polymer. However, since not all initiators absorb water, and initiators that do absorb water do so at different rates, the selection of an initiator based on this property also provides for a degree of control over the degradation of the polymer. For the purposes of this invention, the phrase "suitable for medical application(s)" means that the initiator or accelerator polymerizes the monomer in less than 3 minutes, preferably in less than 2.5 minutes, more preferably in less than 1 minute, and often in less than 45 seconds.

Initiators or accelerators, such as quaternary amines mentioned above, are preferably used in the present invention, but other initiators or accelerators may also be selected by one of ordinary skill in the art without undue experimentation. Such suitable initiators or accelerators may include, but are not limited to, detergent compositions; surfactants: e.g., nonionic surfactants such as polysorbate 20 (e.g., Tween 20® from ICI Americas), polysorbate 80 (e.g., Tween 80® from ICI Americas) and poloxamers, cationic surfactants such as tetrabutylammonium bromide, anionic surfactants such as sodium tetradecyl sulfate, and amphoteric or zwitterionic surfactants such as dodecyldimethyl(3-sulfopropyl)ammonium hydroxide, inner salt; amines, imines and amides, such as imidazole, tryptamine, urea, arginine and povidine; phosphines, phosphites and phosphonium salts, such as triphenylphosphine and triethyl phosphite; alcohols such as ethylene glycol, methyl gallate, ascorbic acid, tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat 336; organometallics such as cobalt naphthenate and manganese acetylacetonate; and radical initiators or accelerators and radicals, such as di-t-butyl peroxide and azobisisobutyronitrile.

Specific compositions of the invention may have various combinations of alkyl ester α-cyanoacrylate monomers and thickeners, plasticizers, colorants, preservatives, heat dissipating agents, stabilizing agents and the like, which will be described in more detail below. Preferably, a composition of this invention has from 65 to 99.9 weight % of an alkyl ester α-cyanoacrylate monomer and is promoted to polymerize by 0.005 to 10 weight % of an initiator or accelerator. More preferably, a composition of this invention has from 80 to 99.9 weight % of an alkyl ester α-cyanoacrylate monomer and is promoted to polymerize by 0.02 to 10 weight % of an initiator or accelerator. Even more preferably, a composition of this invention has 85 to 99.9 weight % of an alkyl ester α-cyanoacrylate monomer, such as 3-(2-Cyano-acryloyloxy)-butyric acid ethyl ester and 3-(2-Cyano-acryloyloxy)-hexanoic acid ethyl ester, and is promoted to polymerize by 0.05 to 5 weight % of an initiator or accelerator, such as domiphen bromide. Compositions of this invention may also include 0 to 25, more preferably 0 to 10, for example 0 to 5 weight % based on a total weight of the composition of at least one of the following: thickeners, plasticizers, colorants, preservatives, heat dissipating agents, stabilizing agents and the like. Of course, other compositions based on other proportions and/or components can readily be prepared according to embodiments of the present invention in light of the present disclosure.

The composition may also optionally include preservatives. A preservative may be selected from among preservatives including, but not limited to, parabens and cresols. For example, suitable parabens include, but are not limited to, alkyl parabens and salts thereof, such as methylparaben, methylparaben sodium, ethylparaben, propylparaben, propylparaben sodium, butylparaben, and the like. Suitable cresols include, but are not limited to, cresol, chlorocresol, and the like. The preservative may also be selected from other known agents including, but not limited to, hydroquinone, pyrocatechol, resorcinol, 4-n-hexyl resorcinol, captan (i.e., 3a,4,7,7a-tetrahydro-2-((trichloromethyl)thio)-1H-isoindole-1,3 (2H)-dione), benzoic acid, benzyl alcohol, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, phenylmercuric compounds such as phenylmercuric borate, phenylmercuric nitrate and phenylmercuric acetate, formaldehyde, and formaldehyde generators such as the preservatives Germall II® and Germall 115® (imidazolidinyl urea, available from Sutton Laboratories, Charthan, N.J.). Other suitable preservatives are disclosed in U.S. patent application Ser. No. 09/430,180, filed Oct. 29, 1999, the entire disclosure of which is hereby incorporated by reference. In embodiments, mixtures of two or more preservatives may also be used.

Monomer compositions of the invention may also include a heat dissipating agent. Heat dissipating agents include liquids or solids that may be soluble or insoluble in the monomer. The liquids may be volatile and may evaporate during polymerization, thereby releasing heat from the composition. Suitable heat dissipating agents may be found in U.S. Pat. No. 6,010,714 to Leung et al., the entire disclosure of which is incorporated herein.

The composition may also optionally include at least one plasticizing agent that imparts flexibility to the polymer formed from the monomer. The plasticizing agent preferably contains little or no moisture and should not significantly affect the stability or polymerization of the monomer. Such plasticizers are useful in polymerized compositions to be used for closure or covering of wounds, incisions, abrasions, sores or other applications where flexibility of the adhesive is desirable. Some thickeners, such as poly-2-ethylhexylcyanoacrylate, may also impart flexibility to the polymer.

Examples of suitable plasticizers include acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate, polydimethylsiloxane, and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

The addition of plasticizing agents in amounts ranging from about 0.1 wt. % to about 25 wt. % provides increased elongation and toughness of the polymerized monomer over polymerized monomers not having plasticizing agents. The composition may also include at least one thickening agent. Suitable thickening agents include, for example, polycyanoacrylates, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene.

The composition may also optionally include at least one thixotropic agent. Suitable thixotropic agents are known to the skilled artisan and include, but are not limited to, silica gels such as those treated with a silyl isocyanate. Examples of suitable thixotropic agents are disclosed in, for example, U.S. Pat. No. 4,720,513, the disclosure of which is hereby incorporated in its entirety.

The composition may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties.

The composition may also optionally include at least one anionic vapor phase stabilizer and/or at least one anionic liquid phase stabilizer. These stabilizing agents inhibit premature polymerization. Such stabilizing agents may also include mixtures of anionic stabilizing agents and radical stabilizing agents. Any mixture of stabilizers is included as long as the mixture does not adversely affect the desired polymerization and absorption of the monomer. Suitable stabilizing agents are disclosed in, for example, U.S. Pat. No. 6,512,023, the entire disclosure of which is hereby incorporated by reference.

Compositions of the present invention are believed to reduce toxicity compared to other cyanoacrylates, such as methyl cyanoacrylate and ethyl cyanoacrylate, due to the absorbable nature of the side-chain structural moieties in the alkyl ester α-cyanoacrylates, such as 3-(2-Cyano-acryloyloxy)-butyric acid ethyl ester (Et-β-HBT-CA) and 3-(2-Cyano-acryloyloxy)-hexanoic acid ethyl ester (Et-β-CPL-CA). However, medical compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites; ammonium sulfite salts; amines; amides; imides; nitriles; carbamates; alcohols; mercaptans; proteins; mixtures of amines, amides, and proteins; active methylene compounds such as cyclic ketones and compounds having a β-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom.

Other examples of formaldehyde level reducing compounds and compositions are exemplified by U.S. Pat. Nos. 6,010,714; 5,624,669; 5,582,834; 5,575,997, the entire disclosures of which are hereby incorporated by reference.

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated in its entirety by reference, discloses such crosslinking agents. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). In accordance with the present disclosure, a catalytic amount of an amine activated free radical initiator, accelerator or rate modifier may be added to initiate polymerization or to modify the rate of polymerization of the cyanoacrylate monomer/crosslinking agent blend.

To improve the adhesion between substrates (e.g. tissue surface) and the compositions of this invention, priming agents may be used to condition the substrate prior to applying in the alkyl ester α-cyanoacrylates. Suitable primers include, but not limited to, ph-modifying agents (e.g. organic or inorganic bases), ionic and non-ionic surfactants, and organic or inorganic salts. Other suitable priming agents can be readily identified by one skilled in the art in light of the present disclosure.

The compositions of this invention may further contain fibrous reinforcement and colorants such as dyes, pigments, and pigment dyes. Examples of suitable fibrous reinforcement include PGA microfibrils, collagen microfibrils, cellulosic microfibrils, and olefinic microfibrils. Examples of suitable colorants include 1-hydroxy-4-[4-methylphenylamino]-9,10 anthracenedione (D+C violet No. 2); disodium salt of 6-hydroxy-5-[(4-sulfophenyl)axo]-2-naphthalene-sulfonic acid (FD+C Yellow No. 6); 9-(o-carboxyphen0yl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-1H-indole-5-sulfonic acid disodium salt (FD+C Blue No. 2); and [phthalocyaninato (2-)] copper. Other modifications to compositions of the present invention are exemplified by U.S. Pat. Nos. 5,624,669; 5,582,834; 5,575,997; 5,514,371; 5,514,372; and 5,259,835; and U.S. patent application Ser. No. 08/714,288, the disclosures of all of which are hereby incorporated in their entirety by reference.

In embodiments of the present invention, the composition may also optionally include at least one biological or therapeutical agent. The variety of biological/therapeutical agents that can be used in conjunction with the plurality of packed particles of the invention is vast. In general, biological/therapeutical agents which may be administered adhesive/sealant compositions of the invention include, without limitation, antiinfectives, such as antibiotics, antimicrobial agents (e.g. Diiodomethyl-p-tolylsulfone, 2,4,4'-Trichloro-2'-Hydroxydiphenyl Ether or combination thereof ) and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, radioactive agents, osteoinductive agents, cystostatics heparin neutralizers, procoagulants and hemostatic agents, such as prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents and synthetic peptides having hemostatic activity.

Compositions of the present invention may be utilized in conjunction with other sealing means. For example, an adhesive may be applied to a wound that has been closed using surgical suture, tape, or staples. Adhesives of the present invention may also be used in conjunction with other sealing means, such as means identified in U.S. Pat. No. 6,014,714, the entire disclosure of which is incorporated herein by reference.

Compositions of the present invention may be applied in single or multiple applications. The adhesives may be applied in a first layer, and after the first layer is allowed to fully or partially polymerize, a subsequent layer may be added. Such a process may be conducted numerous times, depending on the size of the wound and the amount of adhesive applied in each application.

The monomer composition may be packaged in any type of suitable container fabricated from materials including, but not limited to, glass, plastic, metal packages, and film-formed packages. Suitable containers preferably include those into which the compositions may be dispensed and sterilized without unacceptable damage to, or degradation of, the container or the components of the monomer composition. Post-halogenated (e.g., fluourinated) or silanized polymeric barrier layers on at least the monomer-contacting surfaces of the container provide a superior shelf-life for monomer compositions, as disclosed in U.S. patent application Ser. No. 09/430,289, filed Oct. 29, 1999, the entire disclosure of which is hereby incorporated by reference. Glass is especially preferred when sterilization is achieved with dry heat because of the lack of stability of many plastics at temperatures used for dry heat sterilization (typically at least about 140° C.). Examples of types of containers include, but are not limited to, ampoules, vials, syringes, pipettes, and the like.

The present invention also provides a saleable kit for delivering an absorbable cyanoacrylate adhesive to tissue. The kit comprises a saleable package comprising a first container that contains at least one alkyl ester α-cyanoacrylate monomer; and a polymerization initiator or accelerator.

The kit may comprise a second container containing the initiator or accelerator. Or, the first container could have the initiator or accelerator in or on it as long as the initiator or accelerator is not in contact with the monomer prior to the desired use. The initiator or accelerator is selected so that it functions in conjunction with the co-packaged polymerizable monomer composition to initiate polymerization of the monomer or modify (e.g., accelerate) the rate of polymerization for the monomer to form a polymeric adhesive. The proper combination of initiator or accelerator and polymerizable monomer can be determined by one of skill in the art without undue experimentation in light of the present disclosure. The kit may also include a brush, swab or sponge to assist in applying the composition to living tissue. The kit is also preferably sterilized; however, the containers and components may be sterilized separately or together. Preferably, kits and the kit components (including compositions) of the present invention have a sterility level in the range of $10^{-3}$ to $10^{-6}$ Sterility Assurance Level (SAL) and are sterile for surgical purposes. Various designs of such kits are disclosed, for example, in U.S. patent application Ser. No. 09/385,030, filed Aug. 30, 1999, the entire disclosure of which is herein incorporated by reference. The sterilization may be accomplished by techniques known to the skilled artisan, and is preferably accomplished by methods including, but not limited to, chemical, physical, and irradiation methods. Examples of physical methods include, but are not limited to, sterile fill, filtration, sterilization by heat (dry or moist) and retort canning. Examples of irradiation methods include, but are not limited to, gamma irradiation, electron beam irradiation, and microwave irradiation.

In embodiments of the present invention, any suitable applicator may be used to apply the adhesive composition to a substrate. For example, the applicator may include an applicator body, which is formed generally in the shape of a tube having a closed end, an open end, and a hollow interior lumen, which holds a crushable or frangible ampoule. The applicator and its related packaging may be designed as a single-use applicator or as a multi-use applicator. Suitable multi-use applicators are disclosed, for example, in U.S. patent application Ser. No. 09/385,030, filed Aug. 30, 1999, the entire disclosure of which is incorporated herein by reference.

In embodiments of the invention, the applicator may comprise elements other than an applicator body and an ampoule. For example, an applicator tip may be provided on the open end of the applicator. The applicator tip material may be porous, absorbent, or adsorbent in nature to enhance and facilitate application of the composition within the ampoule. Suitable designs for applicators and applicator tips that may be used according to the present invention are disclosed in, for example, U.S. Pat. No. 5,928,611 to Leung and U.S. patent applications Ser. Nos. 09/069,979, filed Apr. 30, 1998, 09/069,875, filed Apr. 30, 1998, 09/479,059, filed Jan. 7, 2000, and 09/479,060, filed Jan. 7, 2000, the entire disclosures of which are incorporated herein by reference.

In embodiments of the present invention, an applicator may contain the initiator or accelerator on a surface portion of the applicator or applicator tip, or on the entire surface of the applicator tip, including the interior and the exterior of the tip. When the initiator or accelerator is contained in or on an applicator tip, the initiator or accelerator may be applied to the surface of the applicator tip or may be impregnated or incorporated into the matrix or internal portions of the applicator tip. Additionally, the initiator or accelerator may be incorporated into the applicator tip, for example, during the fabrication of the tip.

In other embodiments, the initiator or accelerator may be coated on an interior surface of the applicator body and/or on an exterior surface of an ampoule or other container disposed within the applicator body, may be placed in the applicator body in the form of a second frangible vial or ampoule and/or may be otherwise contained within the applicator body, so long as a non-contacting relationship between the polymerizable monomer composition and the initiator or accelerator is maintained until use of the adhesive.

Various designs of applicators and methods for incorporating the initiator or accelerator into the applicator are disclosed in U.S. Pat. No. 5,928,611 to Leung and U.S. patent applications Ser. Nos. 09/069,979, filed Apr. 30, 1998, 09/069,875, filed Apr. 30, 1998, 09/145,200, filed Sep. 1, 1998, the entire disclosures of which are incorporated herein by reference.

Alkyl ester α-cyanoacrylate monomers are particularly useful for medical applications because of the absorbability thereof and of the resultant polymer by living tissue and associated fluids. According to the present invention, the polymerized and applied cyanoacrylate monomer is substantially absorbed in a period of less than 2 years, preferably approximately 2-24 months, more preferably 3-18 months, and most preferably 6-12 months after application to living tissue.

The absorption rate of the polymerized monomer is affected by several factors including the character of the composition and the quantity of the composition applied. For example, regulating the pH of an immediate in vivo environment of the composition may aid in regulating polymer degradation, as disclosed in U.S. patent application Ser. No. 08/714,288, filed Sep. 18, 1996, the entire disclosure of which is hereby incorporated by reference.

The selection of monomer may affect the absorption rate of the resultant polymer, as well as the polymerization rate of the monomer. For example, without being bound by theory, it is believed that the more hygroscopic the initiator, the more rapid will be the degradation of the polymer. Two or more different monomers that have varied absorption and/or polymerization rates may be used in combination to give a greater degree of control over the absorption rate of the resultant polymer, as well as the polymerization rate of the monomer.

Thus, an important aspect of embodiments of the invention lies in the selection of the monomer and initiator to control within relatively narrow and predictable ranges both the polymerization and absorption rates.

The compositions described herein have multiple medical applications. For example, as an internal surgical adhesive and sealant, the adhesive can bond tissue to tissue, tissue to medical device (e.g. meshes, clips and films) and medical device to medical device. As a sealant, the composition can be coated on a tissue, or on a medical device, or on the interface of a medical device with tissue to prevent leaks. The composition can be used to form films in situ that may have applications such as for the prevention of surgical adhesions. The composition can be used to form foams in situ that may have applications such as a filler (e.g. dead space removal, reconstructive and cosmetic surgeries), bulking agents, tissue engineering (e.g. scaffolds) materials and others where foams and sponges are useful. The composition can be formulated so that it is injectable and used to form gels in situ that are localized, and adherent to tissue, staying at the site where they are injected. These may have applications such as a delivery matrix for cells and other biologicals, bioactive agents and pharmaceutical or neutraceutical agents, and as embolization agents, and as means to localize contrasting agents.

As a surgical sealant/adhesive, it can be used as an adjunct to primary wound closure devices, such as staples, sutures, meshes to seal potential leaks of gasses, liquids, or solids. More specifically, the surgical adhesive/sealant may be applied to a tissue as a part of a surgical procedure, in various forms, for example: liquid, powder, film, sponge or foam, impregnated fabric, impregnated sponge or foam, or spray.

As a filler, the monomer composition may be used as a facial, defect or void filler. For example, the composition may be applied in the interstices of an internal void and allowed to polymerize therein, such that the resultant polymer fills the internal cavities and voids, penetrating and conforming to the interstices and pores of the tissue. The composition may be used after a broad number of procedures having potential risk of dead space formation, including, but not limited to, radical mastectomy (i.e. breast and regional lymph nodes removal for cancer treatment), breast reconstruction and augmentation procedure, reconstructive or cosmetic abdominoplasty and liposuction, face-lift, cesarean section and hysterectomy in obese patients, orthopedic procedures on thigh region, incisional hernia repair, lipoma excision, and traumatic lesions, i.e. closed trauma.

EXAMPLES

The present invention will be further understood by reference to the following non-limiting examples.

Example 1A

Synthesis of 3-(2-Cyano-acetoxy)-butyric acid ethyl ester (Et-β-HBT-CAc)

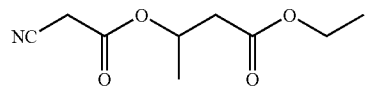

3-(2-Cyano-acetoxy)-butyric acid ethyl ester (Et-β-HBT-CAc)

A mixture of 194.0 g of ethyl-3-hydroxybutyrate, 149.83 g of cyanoacetic acid, and 10.76 g of 4-dimethylaminopyridine (DMAP) was stirred in 1500 ml of $CH_2Cl_2$ in a 3 L three-neck round bottom flask equipped with a mechanical stirrer. About 75 ml of N-N'-dimethylformamide (DMF) was added to the above mixture to make a clear solution. The above solution was chilled in an ice water bath. A separately prepared dicyclohexylcarbodiimide (DCC) solution (363.45 g in 600 ml $CH_2Cl_2$) was added to the above chilled solution by using an addition funnel. White precipitate formed within five minutes after the start of the addition. The reaction mixture was left stirred overnight.

The precipitate was first removed by filtration and the filtrate was evaporated by rotary evaporation to remove solvent. The desired product (3-(2-Cyano-acetoxy)-butyric acid ethyl ester) was obtained by distillation under vacuum twice. A total of 212.5 g (73% yield) of colorless liquid was collected.

$^1$H NMR (CDCl$_3$, δ ppm): 5.39(m, 1H), 4.16(q, 2H), 3.42 (s, 2H), 2.62(m, 2H), 1.37(d, 3H), 1.27(t, 3H) GC-MS: 99.4%.

Boiling point: 100~109° C./0.20~0.27 mmHg.

Example 1B

Synthesis of 3-(2-Cyano-acryloyloxy)-butyric acid ethyl ester (Et-β-HBT-CA)

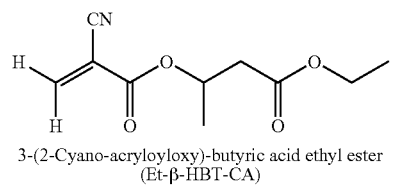

3-(2-Cyano-acryloyloxy)-butyric acid ethyl ester (Et-β-HBT-CA)

A mixture of 39.84 g of 3-(2-Cyano-acetoxy)-butyric acid ethyl ester (Et-β-HBT-CAc), 6.6 g of paraformaldehyde, 0.06 ml of piperidine and 150 ml benzene was stirred in a 250 ml round bottomed flask equipped with a magnetic stir bar. A Dean-Stark trap and a condenser were attached to the reaction flask. The reaction flask was immersed in an oil bath. The reaction mixture was heated to reflux and the reaction was allowed overnight.

The slightly brown colored reaction mixture was evaporated using a rotary evaporator to remove the solvent, yielding a brown colored viscous residue which turned into a solid gel after cooling to room temperature. This solid gel was oligomer of 3-(2-Cyano-acryloyloxy)-butyric acid ethyl ester.

To the above oligomer, 0.20 g of hydroquinone (HQ) and 2.0 g of $P_2O_5$ were added. A simple vacuum distillation was set up where all glassware pieces were previously treated with 5N $H_2SO_4$ solution and dried in a vacuum oven after rinsing by deionized water (DI water). The above mixture of oligomer, hydroquinone and $P_2O_5$ was heated to up to 140° C. to remove low boiling impurities then to above 160° C. in an oil bath under vacuum to carry out the depolymerization. The crude monomer obtained was distilled one more time under vacuum. A total of 8.4 g (20% yield) of colorless liquid was obtained as the final monomer product (3-(2-Cyano-acryloyloxy)-butyric acid ethyl ester).

A very small amount of this monomer product was placed in between two moist fingertips and bonded the fingertips strongly within one minute.

$^1$H NMR (CDCl$_3$, δ ppm): 7.03(s, 1H), 6.60(s, 1H), 5.43 (m, 1H), 4.15(q, 2H) 2.65(m, 2H), 1.40(d, 3H), 1.23(t, 3H) GC-MS: 98.3%.

Boiling point: 114~115° C./0.17 mmHg

Example 2A

Synthesis of 3-(2-Cyano-acetoxy)-hexanoic acid ethyl ester (Et-β-CPL-CAc)

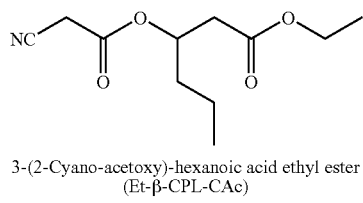

3-(2-Cyano-acetoxy)-hexanoic acid ethyl ester
(Et-β-CPL-CAc)

A mixture of 100.14 g of ethyl-3-hydroxyhexanoate, 63.75 g of cyanoacetic acid, and 4.58 g of 4-dimethylaminopyridine (DMAP) in 625 ml of $CH_2Cl_2$ was stirred in a 2 L three-neck round bottom flask equipped with a mechanical stirrer. About 31 ml of N-N'-dimethylformide (DMF) was added to make a clear solution. The above clear solution was chilled in an ice water bath. A separately prepared dicyclohexylcarbodiimide (DCC) solution (154.75 g in 250 ml $CH_2Cl_2$) was added to the above chilled solution by using an addition funnel. White precipitate formed within five minutes after the start of the addition. The reaction mixture was left stirred overnight.

The precipitate was first removed by filtration and the filtrate was evaporated by rotary evaporation to remove the solvent. The desired product was obtained by distillation under vacuum twice. A total of 86.0 g (61% yield) of colorless liquid was collected.

$^1$H NMR ($CDCl_3$, δ ppm): 5.35(m, 1H), 4.15(q, 2H), 3.42 (s, 2H), 2.62(m, 2H) 1.63(m, 2H), 1.37(m, 2H), 1.24(t, 3H), 0.95(t, 3H) GC-MS: 99.4%.

Boiling point: 115~130° C./~0.43 mmHg.

Example 2B

Synthesis of 3-(2-Cyano-acryloyloxy)-hexanoic acid ethyl ester (Et-β-CPL-CA)

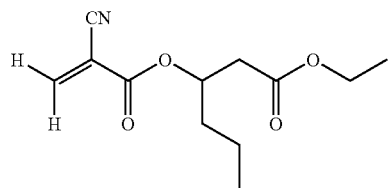

3-(2-Cyano-acryloyloxy)-hexanoic acid ethyl ester
(Et-β-CPL-CA)

Following the same procedures and utilizing the same apparatus as described in example 1B, instead, 45.45 g of 3-(2-Cyano-acetoxy)-hexanoic acid ethyl ester (Et-β-CPL-CAc), 6.6 g of paraformaldehyde, 0.06 ml of piperidine, 0.20 g of HQ, 2.0 g of $P_2O_5$ and 150 ml benzene were used.

As described in example 1B, the crude product was further purified by second distillation under vacuum. A total of 9.6 g (20% yield) of final product was obtained as colorless liquid.

A very small amount of this product was placed in between two moist fingertips and bonded the fingertips strongly within one minute.

$^1$H NMR ($CDCl_3$, δ ppm): 7.03(s, 1H), 6.60(s, 1 H), 5.40 (m, 1 H), 4.15(q, 2H), 2.65(m, 2H), 1.70(m, 2H), 1.38(m, 2H), 1.22(t, 3H), 0.95(t, 3H) GC-MS: 99.0%

Boiling point: 107~114° C./~0.40 mmHg.

Example 3A

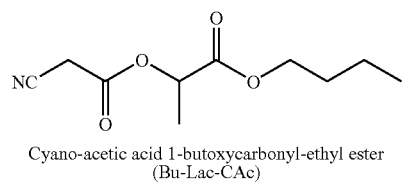

Cyano-acetic acid 1-butoxycarbonyl-ethyl ester
(Bu-Lac-CAc)

Synthesis of cyano-acetic acid 1-butoxycarbonyl-ethyl ester (Bu-Lac-CAc)

A mixture of 292.32 g of butyllactate, 204.14 g of cyanoacetic acid, and 14.66 g of 4-dimethylaminopyridine (DMAP) in 2000 ml of $CH_2Cl_2$ was stirred in a 3 L three-neck round bottom flask equipped with a mechanical stirrer. About 50 ml of N-N'-dimethylformide (DMF) was added to make a clear solution. The above clear solution was chilled in an ice water bath. A separately prepared dicyclohexylcarbodiimide (DCC) solution (495.19 g in 500 ml $CH_2Cl_2$) was added to the above chilled solution by using an addition funnel. White precipitate formed within five minutes after the start of the addition. The reaction mixture was left stirred overnight.

The precipitate was first removed by filtration and the filtrate was evaporated by rotary evaporation to remove the solvent. The desired product was obtained by distillation under vacuum twice. A total of 266.0 g (62% yield) of colorless liquid was collected.

$^1$H NMR ($CDCl_3$, δ ppm): 5.17(q, 1H), 4.19(t, 2H), 3.57(s, 2H), 1.62(m, 2H), 1.56(d, 3H), 1.39(m, 2H), 0.95(t, 3H), GC-MS: 97.0%

Boiling point: 87~97° C./0.10~0.19 mmHg.

Example 3B

Synthesis of 2-Cyano-acrylic acid 1-butoxycarbonyl-ethyl ester (Bu-Lac-CA)

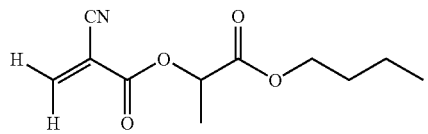

2-Cyano-acrylic acid 1-butoxycarbonyl-ethyl ester
(Bu-Lac-CA)

Following the same procedures and utilizing the same apparatus as described in example 1B, instead, 85.29 g of cyano-acetic acid 1-butoxycarbonyl-ethyl ester (Bu-Lac- CAc), 13.2 g of paraformaldehyde, 0.12 ml of piperidine, 0.40 g of HQ, 4.0 g of $P_2O_5$ and 250 ml benzene were used.

As described in example 1B, the crude product was further purified by second distillation under vacuum. A total of 38.2 g (42% yield) of final product was obtained as colorless liquid.

A very small amount of this product was placed in between two moist fingertips and bonded the fingertips strongly within one minute.

$^1$H NMR ($CDCl_3$, δ ppm): 7.12(s, 1H), 6.68(s, 1H), 5.21(q, 1H), 4.19(t, 2H), 1.62(m, 5H), 1.38(m, 2H), 0.96(t, 3H). GC-MS: 99.2%

Boiling point: 89~99° C./0.31~0.41 mmHg.

Example 4

General Procedure for Lap Shear Testing Using Pig Skin

Fresh pig skin was harvested from the back of the pig within 5 hours post sacrifice. The hair was removed by trimming and shaving to expose a smooth skin surface. The fat attached to the inside skin surface was trimmed away. The skin was cut into 2"×1" coupons and covered by saline moist paper towel before use.

The external surface of the skin was used as bonding surface to prepare the lap shear joint samples.

The coupons were patted dry prior to forming the lap shear joint. About 100 μl of adhesive was deposited to one coupon within ½" from the nearer end and smoothed to cover a ½"×1" area (FIG. 1). The other coupon was placed over the area of the coupon with applied adhesive to form an overlap of ½"×1". A 1 lb weight was placed on top of the overlap area. The joint was allowed to cure for 20~30 min and the strength of the joint was tested as described below.

The strength of the cured joint was tested using an Instron (Model 5544) with a pulling rate of 5 mm/min. The maximum load for the joint to fail was recorded.

Typically, about 10 joint samples were tested for each adhesive. Results are summarized in Table 1.

As shown in Table 1, both the spacer length (n) and the chain lengths of R3 and R4 of the monomer have impacts on the physical performance of the corresponding polymers formed thereof.

Example 5

General Procedure for in vitro Degradation Studies

A 1"×1" Prolene™ mesh (Ethicon, Inc.) was briefly rinsed with 0.5% wt $NaHCO_3$ aqueous solution and patted dry. The mesh was placed on a freshly prepared Agar plate in a petri dish and about 100 mg of monomer adhesive was applied and spread evenly across the mesh. The monomer adhesive was allowed to cure completely overnight with the petri dish covered and sealed with parafilm. The fully cured polymer film formed over the mesh was removed and rinsed with deionized water to remove any Agar attached and patted dry with paper towel. The thickness of the polymer film was about 0.6 mm.

The above film was placed in a hydrolysis chamber with 100 ml deionized water while the temperature of the solution was maintained at 75° C. The pH of the solution was maintained at 7.27 with addition of 0.05N NaOH aqueous solution during the degradation of the polymer film. The amount of the NaOH solution required to maintain pH of 7.27 was recorded as a function of time. The degradation time was defined as the time required for the medium to consume 90% of the total consumed NaOH solution. The degradation time of each polymer was summarized in Table 2.

In addition, the glass transition temperatures (Tg) of the above polymers were also reported in Table 2.

TABLE 2

| In vitro degradation and polymer film properties | | | |
|---|---|---|---|
| Adhesive Polymers | (Invention) Et-β-HBT-CA | (Invention) Et-β-CPL-CA | (Comparative) Bu-Lac-CA |
| Degradation time (h) | 54.6 | 39.4 | 49.4 |
| Glass Transition Temperature (Tg, ° C.) | 32 | −11 | 52 |

TABLE 1

| | | Lap shear data | | | |
|---|---|---|---|---|---|
| Monomer | (Invention) Et-β-HBT-CA | (Invention) Et-β-CPL-CA | (Comparative) Bu-Lac-CA | (Comparative) Et-ε-CPL-CA | (Comparative) Et-α-CPL-CA |
| Load (lb) | 4.09 ± 0.48 | 4.49 ± 0.68 | 4.96 ± 0.67 | 3.68 ± 0.64 | 1.26 ± 0.29 |

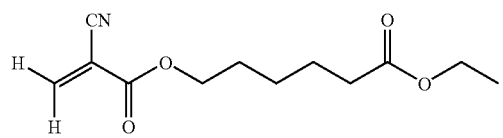

6-(2-Cyano-acryloyloxy)-hexanoic acid ethyl ester
(Et-ε-CPL-CA)

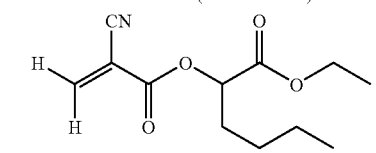

2-(2-Cyano-acryloyloxy)-hexanoic acid ethyl ester
(Et-α-CPL-CA)

As shown in Table 2, the polymers formed from the compositions of the present invention demonstrated Tg lower than body temperature (i.e. 37° C.) which is favorable particularly for medical applications, therefore, it may not be necessary to use plasticizers for the monomer adhesive formulation.

Figure 2:
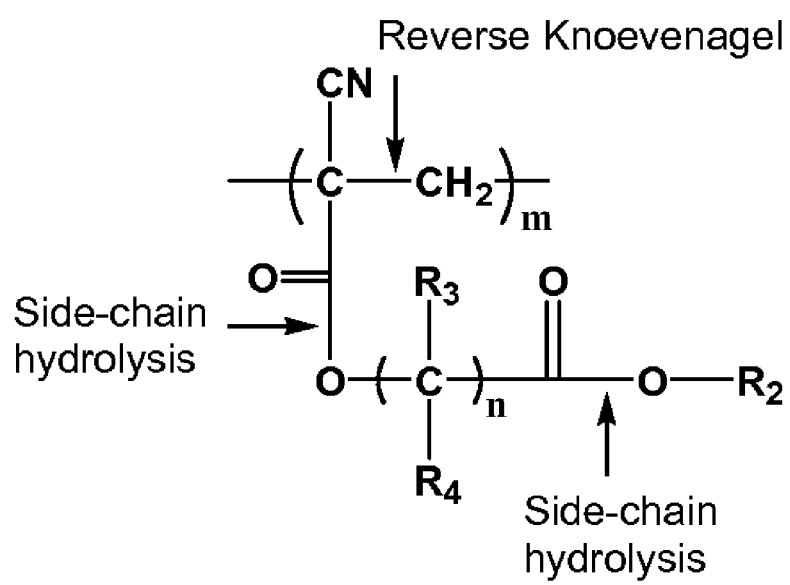
FIG. 2 illustrates polymer degradation mechanisms.

Two mechanisms have been proposed for the degradation of cyanoacrylate polymers via reverse Knoevenagel reaction (F. Leaonard et al., J. Appl. Polym., 10, 259-272, 1966) and side-chain hydrolysis (V. Lenaerts, et al., Biomaterials, 5, 65-68, 1984). The degradation of the title cyanoacrylate polymers may happen through both mechanisms concurrently as illustrated in FIG. 2. There are two possible degradation points via the side-chain mechanism as indicated.

The presence of the hydrolysable side-chain ester functionality is believed to be favorable for the side-chain hydrolysis mechanism that may reduce the generation of formaldehyde as a degradation product, which results from the reverse Knoevenagel reaction mechanism. The side-chain hydrolysis degradation products are believed to include the side-chain ester structure or its fragments such as alcohols and acids, which may not be of great safety concern.

The invention claimed is:

1. A method of treating living tissue, comprising:
applying to living tissue a monomer composition comprising at least one alkyl ester α-cyanoacrylate monomer of the formula:

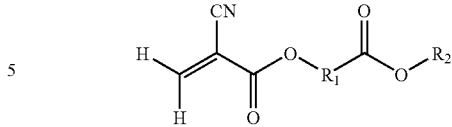

having a spacer R1,

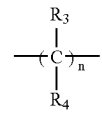

wherein n is from 2 to 12; R3 and R4 are each an alkyl group or a hydrogen, and at least one of R3 or R4 is an alkyl group having from about 1 to 13 carbon atoms; R2 is an alkyl group having from about 1 to 13 carbon atoms; and the combined number of carbon atoms (N) in the spacer R1 is at least n+1.

* * * * *